United States Patent [19]

Delay et al.

[11] Patent Number: 5,057,239

[45] Date of Patent: Oct. 15, 1991

[54] USE OF A SPIRANIC LACTONE AS FRAGRANCE INGREDIENT

[74] Inventors: François Delay, Carouge: Wolfgang K. Giersch; Günther Ohloff, both of Bernex, all of Switzerland

[73] Assignee: Firmenich SA, Geneva, Switzerland

[21] Appl. No.: 281,418

[22] Filed: Dec. 8, 1988

Related U.S. Application Data

[63] Continuation of Ser. No. 70,087, Jul. 7, 1987, abandoned, which is a continuation of Ser. No. 845,081, Mar. 27, 1986, abandoned.

[30] Foreign Application Priority Data

Apr. 19, 1985 [CH] Switzerland ........................ 1692/85

[51] Int. Cl.[5] ........................ C11D 3/50; C11D 9/44; A61K 7/46

[52] U.S. Cl. ................................ 252/174.11; 252/8.6; 252/368; 512/9

[58] Field of Search .................... 252/8.6, 132, 174.11, 252/368; 549/265; 512/9

[56] References Cited

U.S. PATENT DOCUMENTS

| | | | |
|---|---|---|---|
| 2,839,538 | 6/1958 | Nemec | 549/323 |
| 2,960,441 | 11/1960 | van Wessen | 549/265 |
| 3,007,940 | 11/1961 | Shavel | 549/265 |
| 4,519,944 | 5/1985 | Dahill | 252/522 R |

FOREIGN PATENT DOCUMENTS

| | | | |
|---|---|---|---|
| 53-21156 | 2/1978 | Japan | 549/265 |

*Primary Examiner*—Paul Lieberman

*Attorney, Agent, or Firm*—Pennie & Edmonds

[57] ABSTRACT

Spiranic lactone of formula

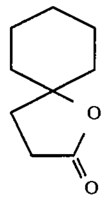

(I)

possesses useful fragrance properties and it can be used advantageously as fragrance ingredient in various consumable materials. It develops warm, spicy, lactonic and coumarinic odor notes.

5 Claims, No Drawings

USE OF A SPIRANIC LACTONE AS FRAGRANCE INGREDIENT

This is a continuation of application Ser. No. 070,087, filed July 7, 1987, now abandoned which is a continuation of application Ser. No. 845,081, filed Mar. 27, 1986, now abandoned.

BRIEF SUMMARY OF THE INVENTION

The present invention relates to the field of perfumery. It provides a method to enhance, improve or modify the odour characters of a consumable material, which method consists in adding to a base selected from a perfume, a soap, a detergent, a fabric softener or a cosmetic product a fragrance effective amount of the spiro-lactone of formula (I)

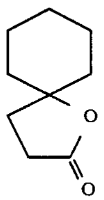

or 1-oxaspiro[4.5]decan-2-one.

The invention also provides a perfume composition containing as fragrance active material the spiro-lactone of formula (I).

The invention provides further a solid or liquid detergent of ionic, anionic, non-ionic or zwitterionic type containing as fragrance active material the spiro-lactone of formula (I).

Finally, the instant invention provides a soap containing as fragrance active material the spiro-lactone of formula (I).

BACKGROUND OF THE INVENTION

Numerous investigations have been published in the scientific literature relating to the synthesis of spiranic lactones. One can revert to the articles of J. Moulines and R. Lalande in Comptes Rend. 261, 1983 (1965) and in Bull. Soc. Chim. France 1075–1080 (1971), or to one of the following papers:

G. I. Nikishin et V. D. Vorob'ev, Isvestiya Akademii Nauk SSSR, Otdelenie Khimicheskikh Nauk 10 (1962) 1874–76;

P. Canonne et al., J. Org. Chem., 46, 3091–7 (1981);

S. Tatsuya et al., Tetrahedron Lett. 21, 5029–32 (1980);

R. M. Jacobson et J. W. Clader, Tetrahedron Lett. 21, 1205–8 (1980);

P. Canonne et al., J. Org. Chem. 45, 1828–35 (1980).

Japanese Patent Application No. 55/76843, published on June 10, 1980, discloses a process for the preparation of cycloaliphatic esters starting from spiranic lactone (I). This application however is mute as to the fragrance characters of the lactone starting material and no suggestion has been made therein to its possible use in the area of perfumery.

European Patent Application published under No. 105157 Apr. 11, 1984 describes a series of spiranic lactones of general formula (II)

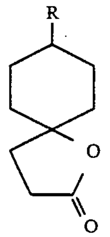

wherein R designates a $C_{1-4}$ alkyl radical, and their utilization as perfume ingredients. The said European application does not mention, nor suggest the possibility of employing lactone (I) in the same area of use.

The table given hereinbelow enumerates the compounds defined by general formula (II) and summarizes their fragrance properties as described in above cited European Patent Application No. 105157.

| R | Odour |
|---|---|
| $CH_3$ | powerful, creamy, lactonic, coumarin direction, weakly cresylic |
| $C_2H_5$ | strong, creamy, lactonic, slightly woody |
| iso-$C_3H_7$ | woody, milk-lactonic type, powdery |
| sec-$C_4H_9$ | peach direction, apricot, lactonic |
| tert-$C_4H_9$ | woody, ambery, weak |

8-Isopropyl-1-oxaspiro[4.5]decan-2-one and 8-ethyl-1-oxaspiro[4.5]decan-2-one were identified by applicant as being the preferred compounds.

THE INVENTION

We have unexpectedly found that 1-oxaspiro[4.5]decan-2-one also possesses interesting and useful fragrance properties and that consequently it can find a broad range of applications for the manufacture of perfumes and perfume bases and for the perfuming of a variety of consumable articles such as soaps, solid and liquid detergents of ionic, anionic, non-ionic or zwitterionic type, fabric softeners, household materials or cosmetics, shampoos and body-deodorizers. When used as active ingredient in polymeric bases or various resins, the lactone of the invention can serve as active principle for odorizing or deodorizing articles such as room-fresheners or closed-spaces deodorizers.

The smell developed by 1-oxaspiro[4.5]decan-2-one can be described as being warm, spicy, lactonic in the direction of rose or tuberose and coumarin.

By comparison with its higher homologue, 8-methyl-1-oxaspiro[4.5]decan-2-one, described in above cited European Patent Application No. 105157, it appears that this latter compound possesses a less elegant and more coumarinic note of coconut type with clearly a fattier nuance. On the contrary, 1-oxaspiro[4.5]decan-2-one develops a lactonic note of flowery type. It possesses a greater fineness and can be utilized at higher concentrations than its corresponding known methyl homologue. This fact is somehow unexpected and surprising inasmuch as for linear aliphatic lactones, of $C_{8-12}$ chain length for instance, which lactones are of common use in perfumery, the aggressiveness of their odour weakens with the increase of the number of carbon atoms. A more detailed comparison between the odour properties of lactone (I) of the invention and its higher homologue will be given in the examples which follow.

The proportions at which lactone (I) can develop the desired fragrance effects can vary within a wide range of values. The skilled perfumer knows by experience that these values vary depending on the nature of the material to be perfumed and of the coingredients in a given perfume composition. Proportions of the order of 5, 10 or even 20% by weight based on the weight of the composition into which it is added can be used without any distortion of the fragrance balance.

Obviously, these values can be lower in the perfuming of articles such as cosmetics, soaps or detergents.

Spiro-lactone (I) can be used according to the invention either by direct addition of the product in its pure isolated form to the articles it is desired to perfume, or typically in admixture with other fragrance ingredients, solvents or supports of current use in perfumery.

The recitation of all functional coingredients is deemed here superfluous; typical examples are abondantly given in the art literature as for example in S. Arctancer, "Perfume and Flavor Materials," Montclair, N.J. (1969). These ingredients can belong to the class of aldehydes, esters, ethers and alcohols; they can be synthetic or of natural origin.

As indicated above, spiro-lactone (I) is a known chemical entity which can be obtained according to prior described methods, for instance by radical addition of an acrylic ester on cyclohexanol in the presence of an organic peroxide. Such a reaction is illustrated by the following reaction scheme:

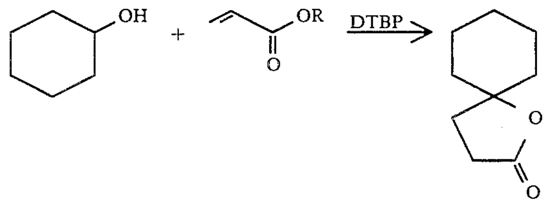

In the above scheme, DTBP, or di-tert-butylperoxide, has been indicated as the active peroxide. Other organic peroxides are known to promote this type of radical reaction and their use in this respect is well known in the art.

In contradistinction to the analogous compounds described in European Patent Application No. 105157, spiro-lactone (I) possesses the advantage of being prepared according to an economical process which uses easily available starting materials, cyclohexanol and methyl acrylate.

The invention is illustrated by not limited to the following examples.

EXAMPLE 1

Fougère type composition

A base composition of fougère type was prepared by mixing the following ingredients (parts by weight):

| | |
|---|---|
| Lavandin oil | 200 |
| Synth. geranium oil | 80 |
| Oak-moss concrete 50%* | 80 |
| Texas cedarwood oil | 60 |
| Benzyl salicylate | 60 |
| Terpenyl acetate | 60 |
| Synth. linalol | 50 |
| Synth. linalol acetate | 40 |
| Patchouli oil | 40 |
| Amyl salicylate | 40 |

-continued

| | |
|---|---|
| Isobutyl benzoate | 30 |
| Terpineol | 20 |
| Aspic oil | 20 |
| Clove oil | 20 |
| Ambrette musk | 20 |
| Musk xylene | 20 |
| Geraniol | 20 |
| Galbanum resin | 10 |
| Phenylacetaldehyde-dimethylacetal | 10 |
| | 880 |

*in diethyl phthalate

Coumarin, a traditional ingredient in such a type of compositions, was omitted in the above base and 12 g of 1-oxaspiro[4.5]decan-2-one was added instead to 88 g of the base ("test" composition).

A "control" composition was prepared by adding to 88 g of the same base, 12 g of 8-methyl-1-oxaspiro[4.5]decan-2-one, the immediate higher homologue of 1-oxaspiro[4.5]decan-2-one, which compound was described in cited European Patent Application No. 105157.

The thus obtained samples were subjected to an odour evaluation by a panel of experienced perfumers. Their finding shows that the "test" composition possessed the desired "fougère" character whereas the "control" composition possessed a lactonic note of coconut type. Their difference is even more pronounced when the respective concentrations of the two said spiro-lactones is doubled. In effect, by adding 24 g of 1-oxaspiro[4.5]decan-2-one, there was obtained a novel composition whose odour remains typically of "fougère" type while the addition to the base of 8-methyl-1-oxaspiro[4.5]decan-2-one gave a composition wherein the coconut character predominates and the original odour of the base is denatured.

EXAMPLE 2

Tuberose composition

A base composition of "tuberose" type was prepared by mixing the following ingredients (parts by weight):

| | |
|---|---|
| Benzyl benzoate | 200 |
| Isoeugenol methyl ether | 110 |
| Methyl anthranilate | 60 |
| Benzyl salicylate | 60 |
| Benzyl alcohol | 60 |
| Farnesol | 50 |
| Linalol | 30 |
| Jasmolactone | 30 |
| Benjoin resin 50%* | 30 |
| Methyl salicylate | 20 |
| Peru balm 50%* | 20 |
| Isoeugenol | 20 |
| Methyl benzoate | 20 |
| Geraniol | 10 |
| Eugenol | 10 |
| Eugenol methyl ether | 10 |
| Benzyl propionate | 10 |
| Phenoxyethyl isobutyrate | 10 |
| Oriental sandalwood oil | 10 |
| Terpineol | 10 |
| Indol 10%* | 10 |
| Dodecyl acetate | 5 |
| Benzyl phenylacetate | 5 |
| | 800 |

*in diethyl phthalate

To such a composition aliphatic lactones such as gamma-octalactone, gamma-nonalactone and gamma-decalactone, typical constituents of this type of compositions, were omitted. 1-Oxaspiro[4.5]decan-2-one (20 g) was added instead to a sample of 80 g of the base to give a "test" composition, whereas a "control" composition was obtained by the addition of 20 g of 8-methyl-1-oxaspiro[4.5]decan-2-one to 80 g of the base. The two compositions thus obtained were subjected to a panel of experienced perfumers who described the odour of the "test" composition as being warm and sweet of tuberose type, whereas the "control" composition developed a sweet-flowery type odour of lactonic character without any tuberose reminiscence.

EXAMPLE 3

Perfuming of soap

100 G of soap chips obtained from an unperfumed sodium soap base prepared from coco oil and tallow were mixed with 1 g of 1-oxaspiro[4.5]decan-2-one until complete homogenization. The resulting soap possessed a flowery odour.

EXAMPLE 4

Perfuming of solid powder detergent

A solid powder detergent base was prepared by mixing the following ingredients (parts by weight):

| | |
|---|---|
| Sodium lin. alkyl-benzene sulphonate (chain length $C_{11-5}$) | 8.0 |
| Ethoxylated tallow alcohol (14EO) | 2.9 |
| Sodium soap (chain length $C_{12-16}$13–26%; $C_{18-22}$74–87%) | 3.5 |
| Sodium triphosphate | 43.8 |
| Sodium silicate | 7.5 |
| Magnesium silicate | 1.9 |
| Carboxymethylcellulose | 1.2 |
| Sodium EDTA | 0.2 |
| Sodium sulphate | 21.2 |
| Water | 9.8 |
| | 100.0 |

The addition to the detergent base of 1-oxaspiro[4.5]decan-2-one at a concentration of 0.1% by weight confers to the base a plaisant flowery odour.

EXAMPLE 5

Perfuming of a fabric softener

A fabric softener base was prepared by mixing the following ingredients (parts by weight):

| Ingredient | Parts by weight | Origin |
|---|---|---|
| Praepagen WK | 10.0 | Hoechst |
| Emulsifier 0120 | 0.5 | Zschimmer & Schwarz |
| Polyglycol 400 | 2.0 | Hoechst |
| Distilled water | 84.4 | |
| Dye: Brilliant Blau R 28032 aqueous sol. at 0.5% | 0.1 | Siegle |
| Sodium chloride in water at 10% | 0.7 | |
| Poromycen F 10 | 0.1 | Kraft |
| Isopropyl alcohol C+ | 2.0 | Shell |
| | 99.8 | |

The addition to a sample of the above indicated softener base of 1-oxaspiro[4.5]decan-2-one at a weight concentration of 0.2%, confers to the base an elegant flowery odour.

EXAMPLE 6

Various consumable materials were perfumed by the addition of 1-oxaspiro[4.5]decan-2-one. The following table shall summarize the results obtained by indicating the dosage used and the effect on odour and colour stability by storage of the perfumed materials for one month in a thermostated oven at 40° C.

| | dosage(1) [%] | stability(2) |
|---|---|---|
| toilet water | 5 | S/N |
| cream | 0.4 | S/N |
| shampoo | 0.5 | S/N |
| aerosol deodorizer | 1.2 | S/N |
| hair lacquer | 0.3 | S/N |
| chlorinated dishwashing powder | 0.2 | fair |

(1)weight concentration of 1-oxaspiro[4.5]decan-2-one
(2)S = stable odour; N = normal colour

What we claim is:

1. Method to modify the odor character of a consumable material in order to confer thereto a spicy, lactonic character in the direction of rose, tuberose and coumarin which comprises adding to a base composition selected from a perfume, a soap, a detergent, a fabric softener or a cosmetic product a fragrance effective amount amount of 1-oxaspiro [4,5] decan-2-one to modify the odor character in the direction of rose, tuberose and coumarin.

2. Method to modify the odor character of a consumable material in order to confer thereto a spicy, lactonic character in the direction of rose, tuberose and coumarin which comprises adding to a base composition selected from a perfume, a soap, a detergent, a fabric softener, or a cosmetic product, 1oxaspiro [4,5] decan-2-one in an amount of between about 0.2 and 20% by weight of the composition to modify the odor character in the direction of rose, tuberose and coumarin.

3. A perfume composition containing as fragrance active material 1-oxaspiro [4,5] decan-2-one in an amount of between about 0.2 and 20% by weight of the composition in order to modify the odor character to confer thereto a spicy, lactonic character in the direction of rose, tuberose and coumarin.

4. A solid or liquid detergent of ionic, anionic, nonionic or zwitterionic type containing as fragrance active material 1-oxaspiro [4,5] decan-2-one in an amount of between about 0.2 and 20% by weight of the composition to modify the odor character to confer thereto a spicy, lactonic character in the direction of rose, tuberose and coumarin.

5. A soap containing as fragrance active material 1-oxaspiro [4,5] decan-2-one in an amount of between about 0.2 and 20% by weight of the composition to modify the odor character to confer thereto a spicy, lactonic character in the direction of rose, tuberose and coumarin.

* * * * *